United States Patent [19]

Chen et al.

[11] Patent Number: 4,503,278

[45] Date of Patent: Mar. 5, 1985

[54] PROCESS FOR CONVERTING CARBOHYDRATES TO HYDROCARBONS

[75] Inventors: Nai Y. Chen, Titusville; Leonard R. Koenig, Trenton, both of N.J.

[73] Assignee: Mobil Oil Corporation, New York, N.Y.

[21] Appl. No.: 574,638

[22] Filed: Jan. 30, 1984

Related U.S. Application Data

[63] Continuation-in-part of Ser. No. 430,461, Sep. 30, 1982, abandoned.

[51] Int. Cl.$^3$ ................................................ C07C 1/20
[52] U.S. Cl. .................................... 585/469; 585/408; 585/640; 585/733
[58] Field of Search ............... 585/408, 469, 639, 646, 585/739, 733

[56] References Cited

U.S. PATENT DOCUMENTS

| 3,998,898 | 12/1976 | Chang et al. | 585/469 |
| 4,300,009 | 11/1981 | Haag et al. | 585/469 |
| 4,306,106 | 12/1981 | Kerr et al. | 585/469 |

*Primary Examiner*—Delbert E. Gantz
*Assistant Examiner*—A. Pal
*Attorney, Agent, or Firm*—A. J. McKillop; M. G. Gilman; J. F. Powers

[57] ABSTRACT

A process is provided for the conversion of carbohydrates such as starch, cellulose and sugar into hydrocarbon products of increased carbon content. Solutions of the carbohydrate are contacted with a crystalline silicate zeolite catalyst such as ZSM-5 at a temperature 300° C. to 650° C. to provide hydrocarbon products which are useful as chemicals or fuels.

9 Claims, 1 Drawing Figure

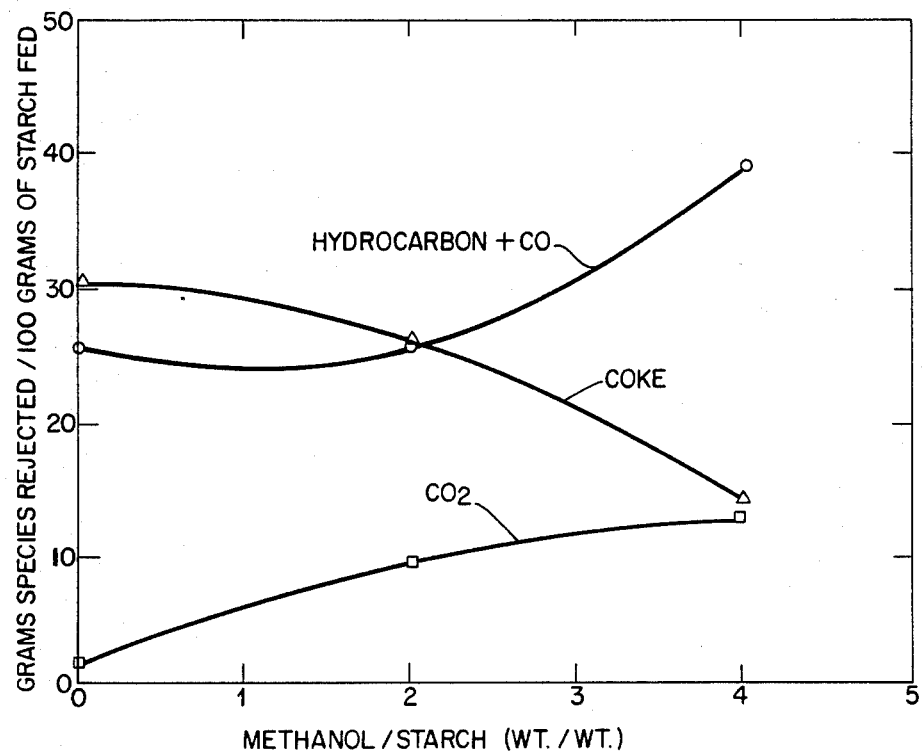

PROCESS FOR CONVERTING CARBOHYDRATES TO HYDROCARBONS

This application is a continuation-in-part of application Ser. No. 430,461, filed Sept. 30, 1982, now abandoned.

BACKGROUND OF THE INVENTION

1. Field of the Invention

This invention relates to a process for the conversion of carbohydrates to hydrocarbons, and more particularly to the conversion of sugars in the presence of a specified crystalline silicate zeolite catalyst.

2. Description of the Prior Art

There is a national interest in finding alternate sources other than petroleum for the production of liquid fuels and chemicals. U.S. Pat. No. 4,313,011, for example, has proposed the recovery of hydrocarbon fuels and chemical feedstocks by thermal conversion of plant biomass in a reducing atmosphere at temperatures of 200° C. to 1000° C. A summary of various processes for conversion of plant materials, including anaerobic digestion, fermentation, gasification and pyrolysis, appears in the publication by Anderson and Tillman entitled "Fuels from Waste", Academic Press, New York, 1977. Catalytic processes also have been developed. U.S. Pat. No. 4,300,009 discloses the conversion of plant or animal anabolites to liquid hydrocarbons in the presence of a crystalline aluminosilicate zeolite catalyst. Other catalytic non-hydrocarbon processes include the conversion of alcohols to olefinic hydrocarbons as described in U.S. Pat. No. 4,148,835; the conversion of lower alcohols and their ethers, such as methanol and dimethyl ether, to a hydrocarbon mixture of ethylene, propylene and mononuclear aromatics as described in U.S. Pat. No. 3,979,472; and the catalytic conversion of mercaptans, sulfides, halides, amines and carbonyl compounds as described in U.S. Pat. No. 4,046,825. In U.S. Pat. No. 3,998,898, mixtures of difficult to convert oxygenates with easy to convert oxygenates such as alcohols, ethers, esters, long chain aldehydes and ketones are co-processed over a crystalline zeolite catalyst to provide aromatic products of gasoline boiling range. Among the compounds that are stated to be difficult to convert are included carboxylic acids and anhydrides, carbohydrates such as starch and sugars, lower glycols, glycerin, and other polyols and short chain aldehydes.

BRIEF SUMMARY OF THE INVENTION

It has been now discovered that carbohydrates such as sugars can be converted into hydrocarbon products by a direct conversion process in which an aqueous solution of sugar is contacted under conversion conditions with a catalyst comprising a crystalline silicate zeolite at temperatures of 300° C. to about 650° C. It has been further discovered that the net hydrocarbon yield of the sugar can be increased by a partially direct conversion in which an aqueous supersaturated solution of the sugar in a lower monohydric alcohol is employed as the charge stock. The conversion process more fully described hereinbelow has been found more economically favorable than other alternative processing schemes for producing gasoline; namely, ethanol fermentation and conversion of ethanol to hydrocarbons (ETG) or gasification, water gas shift, methanol synthesis and conversion of methanol to hydrocarbons (MTG).

BRIEF DESCRIPTION OF THE DRAWING

The FIGURE illustrates the effect of methanol/starch ratio on product distribution.

DETAILED DESCRIPTION OF THE INVENTION

The starting mixtures used for purposes of the invention are characterized as having an overall effective hydrogen to carbon ratio of about 0 to 2.0. Carbohydrates, by definition, have the general formula $C_n(H_2O)_n$ and an $(H/C)_{eff}$ of zero. The effective hydrogen to carbon ratio, abbreviated herein as $(H/C)_{eff}$ is calculated from the gross composition as follows:

$$(H/C)_{eff} = \frac{(H - 2(O) - 3N - N - 2S)}{C}$$

where H, C, O, N, S are the relative atom ratios of hydrogen, carbon, oxygen, nitrogen and sulfur as determined by elemental analysis of the feed on an anhydrous basis.

To illustrate the computation of $(H/C)_{eff}$, i.e., the effective hydrogen to carbon ratio, of sugar, for example, an elementary analysis of a sample, on an anhydrous basis, would give the approximate empirical formula with no significant nitrogen or sulfur content as follows:

$$C_{12}H_{22}O_{11}$$

Inserting the appropriate values in the above equation gives:

$$(H/C)_{eff} = \frac{22 - 22 - 0 - 0}{12} = \frac{0}{12} = 0.$$

Typical examples of suitable starting mixtures in the practice of the invention are:

|  | Analysis | $(H/C)_{eff}$ |
|---|---|---|
| Sugar | $C_{12}H_{22}O_{11}$ | 0 |
| Starch, cellulose | $(C_6H_{10}O_5)_n$ | 0 |
| Alcohol | $C_nH_{2n+2}O$ | 2 |

Although materials having a $(H/C)_{eff}$ of less than 1 can be used in the production of hydrocarbons, it is preferred to utilize charge stock mixtures having an overall effective hydrogen to carbon ratio of at least 1.2, preferably about 1.3 to 1.6, to avoid catalyst deactivation and low yield of useful hydrocarbon products. In the practice of the invention, increased hydrogen to carbon ratios may be obtained by forming an aqueous supersaturated solution of the carbohydrate starting material in a lower monohydric alcohol such as methanol, ethanol, n-propanol, isopropanol, n-butanol, sec-butanol, isobutanol or mixtures thereof. Thus, by heating a 2/1 or 4/1 solution of methanol to glucose in water at temperatures of about 60° C. for 12 hours, stable supersaturated homogeneous solutions are obtained which have an $(H/C)_{eff}$ of 1.3 and 1.6, respectively. Referring to the FIGURE, the effect of alcohol concentration is shown over a range of 0 to 4:1 weight ratio of methanol to hydrolyzed starch at 510° C. The data show a consistent trend that as the concentration of methanol is increased, the yield of coke decreases and the yield of hydrocarbon, CO and $CO_2$ increases. As shown hereinafter, the conversion of a stable supersaturated homogeneous carbohydrate/alcohol solution obtained from two normally immiscible components, alcohol and sugar, is spectacularly successful and quite unexpected.

The starting mixtures employed for purposes of the invention include the crystalline compounds identified as sugars and the non-crystalline compounds such as starches, celluloses and allied products which can be hydrolyzed to sugars with mineral acids and/or enzyme(s). The preferred starting materials are monosaccharides and particularly the pentoses such as arabinose, xylose, ribose, etc., and hexoses such as dextrose (also known as glucose), mannose, galactose, fructose and sorbose, etc. Disaccharides such as sucrose, maltose and lactose can be employed but are less preferred because of molecular size. The disaccharides and polysaccharides $(C_6H_{10}O_5)_x$ such as starch, cellulose, dextrin, pectins, etc., will yield more than one molecule of monosaccharide upon hydrolysis and can be employed as such for purposes of the invention.

The sugars can be employed as an aqueous solution ranging from 10 to 90 weight percent sugar or as an aqueous supersaturated solution in a lower monohydric alcohol in weight ratios of alcohol to sugar ranging from 1 to 10 parts of alcohol per part of sugar. When employing an aqueous solution of sugar in the monohydric alcohol, the water to carbohydrate weight ratio (wt./wt.) is at least 0.3 and preferably at least 0.4.

The particular crystalline zeolite catalyst utilized herein may be any member of the novel class of zeolites now to be described. Although these zeolites have unusually low alumina contents, i.e., high silica to alumina ratios, they are very active even when the silica to alumina ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g., of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning with oxygen-containing gas such as air.

An important characteristic of the crystal structure of this class of zeolites is that it provides constrained access to and egress from the intracrystalline free space by virtue of having an effective pore size intermediate between the small pore Linde A and the large pore Linde X, i.e., the pore windows of the structure have about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type zeolites useful in this invention possess, in combination: a silica to alumina mole ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina ratio of at least 12 are useful, it is preferred to use zeolites having higher ratios of at least about 30. Such zeolites, after activation, acquire an intracrystalline sorption capacity for normal hexane which is greater than that for water, i.e., they exhibit "hydrophobic" properties. It is believed that this hydrophobic character is advantageous in the present invention.

The zeolites useful in this invention have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although in some instances excessive puckering of the rings or pore blockage may render these zeolites ineffective. 12-membered rings usually do not offer sufficient constraint to produce the advantageous conversions, although the puckered 12-ring structure of TMA offretite shows constrained access. Other 12-ring structure may exist which, due to pore blockage or to other cause, may be operative.

Rather than attempt to judge from crystal structure whether or not a zeolite possesses the necessary constrained access to molecules larger than normal paraffins, a simple determination of the "Constraint Index" as herein defined may be made by passing continuously a mixture of an equal weight of normal hexane and 3-methylpentane over a small sample, approximately one gram or less, of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature is adjusted between 550° F. and 950° F. to give an overall conversion between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to total hydrocarbon mole ratio of 4:1.

After 20 minutes on stream, a sample of the effluent is taken and analyzed, most conveniently by gas chromatography, to determine the fraction remaining unchanged for each of the two hydrocarbons. The "Constraint Index" is calculated as follows:

$$\text{Constraint Index} = \frac{\log_{10} (\text{fraction of n-hexane remaining})}{\log_{10} (\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical zeolites are:

| CAS | C.I. |
|---|---|
| ZSM-4 | 0.5 |
| ZSM-5 | 8.3 |
| ZSM-11 | 8.7 |

| CAS | C.I. |
| --- | --- |
| ZSM-12 | 2 |
| ZSM-23 | 9.1 |
| ZSM-35 | 4.5 |
| ZSM-38 | 2 |
| TMA Offretite | 3.7 |
| Beta | 0.6 |
| H—Zeolon (mordenite) | 0.4 |
| REY | 0.4 |
| Amorphous Silica—Alumina | 0.6 |
| Erionite | 38 |

The above described Constraint Index is an important and even critical definition of those zeolites which are useful in the instant invention. The very nature of this parameter and the recited technique by which it is determined, however, admit of the possibility that a given zeolite can be tested under somewhat different conditions and thereby have different Constraint Indexes. Constraint Index seems to vary somewhat with severity of operation (conversion) and the presence or absence of binders. Therefore, it will be appreciated that it may be possible to so select test conditions to establish more than one value in the range of 1 to 12 for the Constraint Index of a particular zeolite. Such a zeolite exhibits the constrained access as herein defined and is to be regarded as having a Constraint Index of 1 to 12. Also contemplated herein as having a Constraint Index of 1 to 12 and therefore within the scope of the novel class of highly siliceous zeolites are those zeolites which, when tested under two or more sets of conditions within the above-specified ranges of temperature and conversion, produce a value of the Constraint Index slightly less than 1, e.g., 0.9, or somewhat greater than 12, e.g., 14 or 15, with at least one other value of 1 to 12. Thus, it should be understood that the Constraint Index value as used herein is an inclusive rather than an exclusive value. That is, a zeolite when tested by any combination of conditions within the testing definition set forth hereinabove to have a Constraint Index of 1 to 12 is intended to be included in the instant catalyst definition regardless that the same identical zeolite tested under other defined conditions may give a Constraint Index value outside of 1 to 12.

The class of zeolites defined herein is exemplified by ZSM-5, ZSM-11, ZSM-12, ZSM-23, ZSM-35, ZSM-38, and other similar materials. U.S. Pat No. 3,702,886 describing and claiming ZSM-5 is incorporated herein by reference.

ZSM-11 is more particularly described in U.S. Pat. No. 3,709,979, the entire content of which is incorporated herein by reference.

ZSM-12 is more particularly described in U.S. Pat. No. 3,832,449, the entire content of which is incorporated herein by reference.

ZSM-23 is more particularly described in U.S. Pat. No. 4,076,842, the entire content of which is incorporated herein by reference.

ZSM-35 is more particularly described in U.S. Pat. No. 4,016,245, the entire content of which is incorporated herein by reference.

ZSM-38 is more particularly described in U.S. Pat. No. 4,046,859, the entire content of which is incorporated herein by reference.

The specific zeolites described, when prepared in the presence of organic cations, are substantially catalytically inactive, possibly because the intracrystalline free space is occupied by organic cations from the forming solution. They may be activated by heating in an inert atmosphere at 1000° F. for one hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 1000° F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite, and clinoptilolite. The preferred crystalline aluminosilicates are ZSM-5, ZSM-11, ZSM-12, ZSM-23, ZSM-35, and ZSM-38, with ZSM-5 being particularly preferred.

In a preferred aspect of this invention, the zeolites hereof are selected as those having a crystal framework density, in the dry hydrogen form, of not less than about 1.6 grams per cubic centimeter. It has been found that zeolites which satisfy all three of these criteria are most desired for several reasons. When hydrocarbon products or by-products are catalytically formed, for example, such zeolites tend to maximize the production of gasoline boiling range hydrocarbon products. Therefore, the preferred zeolites of this invention are those having a Constraint Index as defined above of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space. It is possible that the unusual sustained activity and stability of this class of zeolites is associated with its high crystal anionic framework density of not less than about 1.6 grams per cubic centimeter. This high density must necessarily be associated with a relatively small amount of free space within the crystal, which might be expected to result in more stable structures. The free space, however, is important as the locus of catalytic activity.

Crystal framework densities of some typical zeolites including some which are not within the purview of this invention are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Lauminite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 0.5 percent by weight may be used. Thus, the original alkali metal of the zeolite may be replaced by ion exchange with cobalt, but other suitable ions of Groups IB to VIII of the Periodic Table, including, by way of example, nickel, copper, zinc, palladium, calcium or rare earth metals, also may be present.

In practicing the process of the invention, it may be desirable to incorporate the zeolite in another material resistant to the temperatures and other reaction conditions employed. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the subbentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix materials, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided zeolite and inorganic oxide gel matrix may vary widely with the zeolite content ranging from between about 1 to about 99 percent by weight and more usually in the range of about 5 to 80 percent by weight of the composite. A particularly suitable combination is one containing about 40 weight percent of the zeolite in 60 weight percent of a relatively inactive silica alumina matrix.

Contacting the carbohydrate solution or aqueous mixture thereof with alcohol is carried out in a fluidized bed operated in a transport fashion such that the catalyst, is circulated between a reaction zone and a regeneration zone as is currently practiced in the fluid catalytic cracking of petroleum gas oils. The catalyst must be in finely divided form which can be fluidized by the lifting action of the feed vapors and may be held in fluidized form, if desired, by a stream of relatively inert gas such as steam, $CO_2$, CO, flue gas, $N_2$, He or methane. The carbohydrate feed is passed over the catalyst at a rate of 0.2–5.0 WHSV (weight hourly space velocity), preferably at a space velocity of 0.5 to 2.5 WHSV, calculated on the pounds of anhydrous carbohydrate fed per hour of catalyst in the bed. For purposes of this invention, the carbohydrate feed is contacted with the catalyst at a pressure of 1 to 50 atmospheres absolute and preferably at a pressure of 0 to 150 psig (pounds per square inch gauge). The conversion is carried out at a temperature of 300° to about 650° C. and preferably within the range of 400° to 550° C.

In general, the effluent from the conversion step consists of a gas phase product, a two-phase liquid product and coke deposit on the catalyst. A minor stream of catalyst may be periodically withdrawn from the catalyst bed for passage to a catalyst regeneration zone where it is regenerated on a continuous or intermittent basis. In the catalyst regeneration zone, carbonaceous deposits are burned or removed from the catalysts by passing a gas such as air or other suitable oxygen-containing gas over the catalyst, preferably for 1 to 30 minutes, at a temperature within the range of 400° C. to about 760° C. at pressures within the range of 0 to 100 psig, preferably less than 50 psig.

The following examples illustrate the best mode now contemplated for carrying out the invention.

EXAMPLES

The direct conversion of sugar and hydrolyzed starch was carried out in a cyclic fluid bed reactor at a temperature of 510° C. at a weight hourly space velocity (WHSV) of 1.9 to 2.1. The conversion cycle was for 10 minutes using a 40% HZSM-5 catalyst dispersed in a silica-alumina matrix. The catalyst was steamed 24 hours at 850° F. to an alpha value ($\alpha$) of 40 (based on zeolite) and sized to 60–80 mesh particles. The alpha value reflects the relative activity of the catalyst with respect to a high activity silica-alumina cracking catalyst and is more fully described in the Journal of Catalysis, Vol. VI, pages 278–287, 1966. The catalyst bed contained 35 cc (13.7 g) of catalyst mixed with 15 cc (14.2 g) 80–120 mesh vycor. A summary of the results using a 50% aqueous solution of various sugars is presented in the table below. On the basis of carbon fed, about 20% of the monosaccharide carbon, including the 5-carbon atom sugar xylose and 6-carbon atom sugars glucose and hydrolyzed starch, was converted to hydrocarbons. On the basis of CO as a premium product up to 60% of the carbon can be recovered as premium products.

TABLE I

| | DIRECT CONVERSION OF CARBOHYDRATES | | | | | | | |
|---|---|---|---|---|---|---|---|---|
| | Mass Balance | | | | Carbon Balance | | | |
| | Xylose | Glucose | Hydrolyzed Starch | Sucrose | Xylose | Glucose | Hydrolyzed Starch | Sucrose |
| Example | 145 | 128 | 126 | 140 | 145 | 128 | 126 | 140 |
| Hydrocarbons | 10.0 | 8.2 | 8.9 | 4.4 | 21.8 | 18.0 | 17.8 | 9.0 |
| CO | 33.3 | 18.9 | 16.8 | 32.8 | 35.6 | 20.3 | 16.2 | 33.5 |
| $CO_2$ | 3.7 | 3.6 | 1.5 | 5.6 | 2.6 | 2.5 | 2.9 | 3.6 |
| Coke | 16.8 | 24.9 | 30.4 | 23.8 | 40.0 | 59.2 | 65.1 | 53.9 |
| $H_2O$ | 36.2 | 44.4 | 42.4 | 33.4 | — | — | — | — |

In Table II below, various carbohydrate sugars were converted to hydrocarbon by passing a stable aqueous supersaturated homogeneous solution of sugar in crude methanol over a ZSM-5 type catalyst. The feed materials were prepared as follows:

Methanol Solution of Carbohydrates

Example: a 4/1 solution of methanol to glucose was prepared by adding 74.21 g of methanol to 18.24 g of glucose in 7.55 g of $H_2O$. The vessel was sealed and placed on a stirring hot plate at $\approx 60°$ C. for $\approx 12$ hours. The feed remained in homogeneous solution for $\approx 8$ hours at room temperature, much longer at elevated temperatures.

Hydrolysis of Starch and Methanol Solution of Hydrolyzed Starch

Example: a 4/1 solution of methanol to starch was prepared by placing 18.24 g of starch in 7.55 g of 2N HCL into a container which was then sealed and placed on a stirring hot plate at $\approx 60°$ C. A clear, tawny liquid was formed in about 5 hours. Upon cooling, 74.21 g of methanol were added to the carbohydrate/acid solution, the container resealed and placed on a stirring hot plate heated to about $60°$ C. for an additional hour to ensure homogeneity. The solutions were used as such without further treatment.

The conversion of the above solutions was carried out in the same manner described above using the same catalyst and temperature at a weight hourly space velocity (WHSV) of 1.4 to 1.8. As shown below, methanol solutions of glucose and hydrolyzed starch showed the largest increase in net hydrocarbon yield. The hydrocarbon yield from the xylose/methanol solution is similar to that of the hexose while the sucrose/methanol solution increased in hydrocarbon yield but remained lower than that of the monosaccharides.

Comparison With Other Biomass Conversion Processes

Since methanol can be produced from carbohydrates indirectly via the gasification route, the methanol/carbohydrate conversion process may be defined as a partially direct biomass conversion process. The efficiency of mass and energy recovery of this partially direct conversion process may be compared with known indirect process schemes producing similar product slates, viz., mass recovery efficiencies:

(a) ethanol fermentation and conversion of ethanol to hydrocarbons (ETG)
(b) gasification, water gas shift, methanol synthesis and conversion of methanol to hydrocarbons (MTG)

The theoretical yield of hydrocarbons may be estimated from the following stoichiometric equations:

Thus, for ethanol fermentation:

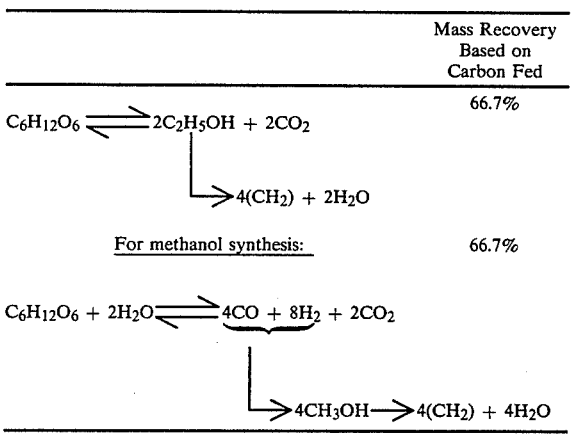

Thus theoretical maximum yield of 66.7% based on carbon fed can be expected from either of the two alternative schemes.

In the case of the partially direct conversion process, the best result was Example 148 which yielded 45.7 weight percent carbon as hydrocarbons, 13.7 weight percent as CO and 33.4 weight percent as coke. Adding

TABLE II

| | CONVERSION OF METHANOL/CARBOHYDRATES | | | | | | | |
|---|---|---|---|---|---|---|---|---|
| | Mass Balance (net carbohydrate) | | | | Carbon Balance (net carbohydrate) | | | |
| | Xylose | Glucose | Hydrolyzed Starch | Sucrose | Xylose | Glucose | Hydrolyzed Starch | Sucrose |
| Example | 144 | 148 | 125 | 141 | 144 | 148 | 125 | 141 |
| Hydrocarbons | 18.6 | 19.0 | 18.6 | 7.9 | 41.6 | 45.7 | 42.2 | 22.0 |
| CO | 13.2 | 12.8 | 20.3 | 6.0 | 14.1 | 13.7 | 19.6 | 6.1 |
| $CO_2$ | 7.2 | 10.4 | 12.6 | 10.8 | 4.9 | 7.2 | 7.8 | 7.0 |
| Coke | 16.6 | 14.0 | 14.3 | 28.7 | 39.4 | 33.4 | 30.4 | 64.9 |
| $H_2O$ | 44.4 | 43.8 | 34.2 | 46.6 | — | — | — | — | to the hydrocarbons, the theoretical yield of hydrocarbons from CO and coke estimated from similar stoichiometric equations:

$$3CO + 2H_2O \longrightarrow CH_3OH + 2CO_2 \quad 33.3\%$$
$$\longrightarrow (CH_2) + 2H_2O$$

$$3C + 4H_2O \longrightarrow 2CH_3OH + CO_2 + H_2O \quad 66.7\%$$
$$\longrightarrow 2(CH_2)$$

gives an estimated total carbon recovery for the partially direct conversion process of 72.5%, which is higher than the theoretical yield of the indirect processes. This is possible when carbon is recovered as $CH_x$ where x is less than two as is the case with the partially direct conversion process. Of course, actual carbon recovery would be lower. For example, the fermentation process has a practical efficiency of about 90 percent; gasification efficiency is generally lowered by the byproduct methane, which has a theoretical 50 percent carbon recovery and the amount of carbon burned to supply heat.

A detailed product analysis for Example 148 is set forth below in Table III and compared with the results obtained when methanol alone was converted over the same catalyst at a temperature of 510° C. and space velocity of 2.1.

TABLE III

DETAILED PRODUCT ANALYSIS

| Example Feed Component, Wt. % | 146 Methanol | 148 Methanol/Glucose | Difference |
|---|---|---|---|
| Methane | 0.84 | 1.71 | +0.87 |
| Ethane | 0.74 | 5.49 | +4.75 |
| Ethylene | 4.01 | 0.48− | −3.53 |
| Propane | 0.89 | 8.77 | +7.88 |
| Propylene | 12.58 | 0.37 | −12.21 |
| Butanes | 1.69 | 0.22− | −1.47 |
| Butenes | 2.84 | 1.80 | −1.04 |
| Pentanes | 1.08 | 0.84+ | −0.24 |
| Pentenes | 3.69 | 2.19 | −1.50 |
| Hexanes | 0.99 | 3.25 | +2.26 |
| Hexenes | 2.76 | 0.01 | −2.75 |
| Heptanes | 0.11 | 0 | −0.11 |
| Heptenes | 0.42 | 0 | −0.42 |
| Octanes | 0.09 | 0.18 | +0.09 |
| Octenes | 0.33 | 0.35 | +0.02 |
| Nonanes | 0 | 0 | 0 |
| Nonenes | 0.07 | 0.04 | −0.03 |
| Benzene | 0.23 | 0.88 | +0.65 |
| Toluene | 1.09 | 2.40 | +1.31 |
| $C_8$ Aromatics | 4.62 | 7.40 | +2.78 |
| $C_9$ Aromatics | 3.00 | 9.30 | +6.30 |
| $C_{10}$ Aromatics | 0.71 | 1.93 | +1.22 |
| $C_{11}$ Aromatics | 0.15 | 0.26 | +0.11 |
| $C_{12}$ Aromatics | 0 | 0.20 | +0.20 |
| Other Aromatics | 0.05 | 0.43 | +0.38 |
| CO | 0 | 3.18 | +3.18 |
| $CO_2$ | 0.27 | 2.58 | +2.31 |
| Water | 56.12 | 67.12 | +11.00 |
| Coke | 0.63 | 3.49 | +2.86 |
| Total | 100.00 | 124.87 | 24.87 |
| $C_5^+$ % Total Hydrocarbons | 45.1 | 61.2 | |

The potential of the carbohydrate conversion process described herein may be increased by incorporating other organic materials in the supersaturated solution and converting the same to hydrocarbons. Such materials as ethers, acetals, esters, acids, paraffins, short chain aldehydes, carbonyls, and the like, may be co-processed with the supersaturated solutions to provide aromatic rich hydrocarbon products.

What is claimed is:

1. A process for the conversion of carbohydrates to hydrocarbons which comprises contacting an aqueous homogeneous saturated solution of carbohydrates in a lower monohydric alcohol having a water to carbohydrate weight ratio (wt./wt.) of at least 0.3 under conversion conditions at temperatures of about 300° C. to 650° C., space velocities of 0.2 to 5.0 WHSV and pressures of 1 to 50 atmospheres absolute with a crystalline silicate zeolite catalyst having a constraint index of about 1 to 12 and a dried crystal density in the hydrogen form not substantially less than about 1.6 grams per cubic centimeter, and thereafter recovering a hydrocarbon product of increased carbon content.

2. The process of claim 1 wherein the carbohydrate solution has an effective hydrogen to carbon ratio of about 0 to 2.0.

3. The process of claim 1 wherein the carbohydrate solution has an effective hydrogen to carbon ratio of about 1.3 to 1.6.

4. The process of claim 2 wherein the carbohydrate solution is the hydrolysis product of a polysaccharide.

5. The process of claim 4 wherein the polysaccharide is starch or cellulose.

6. The process of claim 2 or 3 wherein the crystalline silicate zeolite catalyst is ZSM-5.

7. The process of claim 6 wherein the catalyst is dispersed in a matrix.

8. The process of claim 2 wherein said carbohydrate is sugar.

9. The process of claim 8 wherein the carbohydrate is a monosaccharide or disaccharide.

* * * * *

UNITED STATES PATENT AND TRADEMARK OFFICE
CERTIFICATE OF CORRECTION

PATENT NO. : 4,503,278

DATED : March 5, 1985

INVENTOR(S) : N. Y. Chen and L. R. Koening

It is certified that error appears in the above-identified patent and that said Letters Patent is hereby corrected as shown below:

Col. 2, lines 16 and 17, "$(H/C)_{eff} = \frac{(H-2(O)-3N-N-2S)}{C}$"

should be $$--(H/C)_{eff} = \frac{(H-2(O)-3N-2S)}{C}--.$$

Signed and Sealed this

Twenty-second Day of October 1985

[SEAL]

Attest:

DONALD J. QUIGG

Attesting Officer

*Commissioner of Patents and Trademarks—Designate*